United States Patent [19]

Paterson

[11] Patent Number: 4,632,109

[45] Date of Patent: Dec. 30, 1986

[54] CIRCUITRY FOR PROCESSING REQUESTS MADE FROM THE STERILE FIELD OF A SURGICAL PROCEDURE TO CHANGE THE OUTPUT POWER LEVEL OF AN ELECTROSURGICAL GENERATOR

[75] Inventor: William G. Paterson, Longmont, Colo.

[73] Assignee: Valleylab, Inc., Boulder, Colo.

[21] Appl. No.: 680,966

[22] Filed: Dec. 11, 1984

[51] Int. Cl.$^4$ .............................................. A61B 17/39
[52] U.S. Cl. ............................ 128/303.14; 128/303.17
[58] Field of Search .................... 128/6, 303.1, 303.12, 128/303.13, 303.14, 303.15, 303.17, 303.18

[56] References Cited

U.S. PATENT DOCUMENTS

| 3,439,680 | 4/1969 | Thomas, Jr. | 128/303.1 |
| 4,334,539 | 6/1982 | Childs et al. | 128/303.17 |
| 4,407,272 | 10/1983 | Yamaguchi | 128/6 |

FOREIGN PATENT DOCUMENTS

| 2820908 | 11/1978 | Fed. Rep. of Germany | 128/303.1 |
| 2803275 | 8/1979 | Fed. Rep. of Germany | 128/303.13 |
| 3143421 | 5/1982 | Fed. Rep. of Germany | 128/303.1 |

Primary Examiner—Lee S. Cohen
Assistant Examiner—David Shay
Attorney, Agent, or Firm—Gerald J. Ferguson, Jr.; Michael P. Hoffman; Ronni S. Malamud

[57] ABSTRACT

An electrosurgical generating system including an electrosurgical generator; a handpiece including an active electrode connected to the generator for applying electrosurgical current from the generator to a patient; and an initializing device or circuit for making an initial determination as to whether the handpiece includes power changing switches for changing the level of the output power delivered from the generator to the patient. Assuming the handpiece does include such switches, circuitry is also disclosed for limiting the amount the power can be increased or decreased from the handpiece. Also circuitry is disclosed for effecting the power increase or decrease in incremental steps.

9 Claims, 9 Drawing Figures

FIG. 1
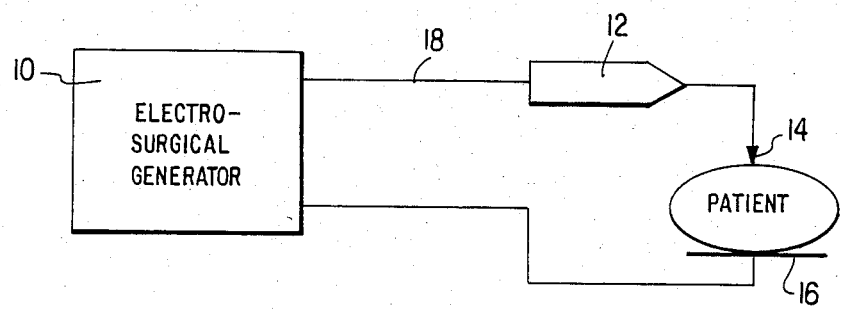
FIG. 2
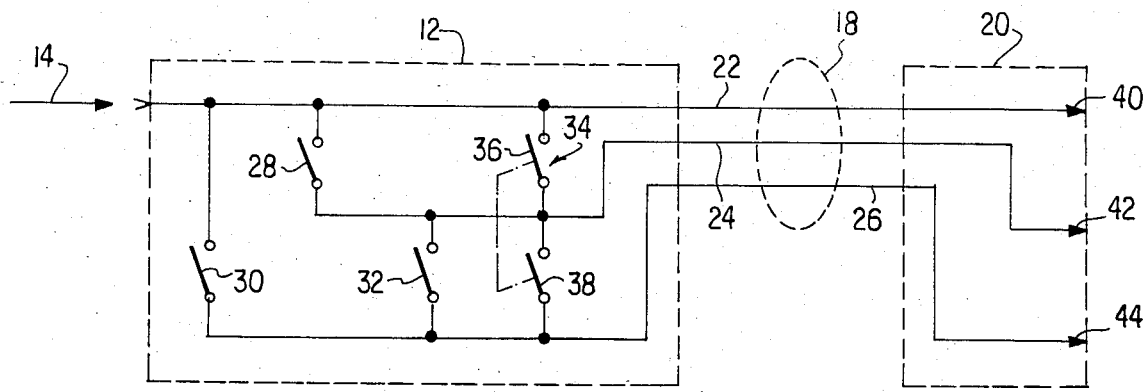
FIG. 4
| ACTUATION | CONNECTION | $\overline{OUT\ 1}$ | $\overline{OUT\ 2}$ | $\overline{OUT\ 3}$ |
|---|---|---|---|---|
| NONE | NONE | 1 | 1 | 1 |
| CUT SW 30 | ACTIVE · CUT SW | 1 | ∅ | ∅ |
| COAG SW 28 | ACTIVE · COAG SW | ∅ | 1 | 1 |
| UP SW 32 | CUT SW · COAG SW | 1 | 1 | ∅ |
| DOWN SW 36 | ACTIVE · CUT SW · COAG SW | ∅ | ∅ | ∅ |

CIRCUITRY FOR PROCESSING REQUESTS MADE FROM THE STERILE FIELD OF A SURGICAL PROCEDURE TO CHANGE THE OUTPUT POWER LEVEL OF AN ELECTROSURGICAL GENERATOR

CROSS-REFERENCE TO RELATED APPLICATION

This application is related to a co-pending U.S. application filed on even date herewith by David W. Newton entitled "Method and Apparatus for Changing the Output Power Level of an Electrosurgical Generator While Remaining in the Sterile Field of an Electrosurgical Procedure".

BACKGROUND OF THE INVENTION

This invention relates to electrosurgery and in particular to apparatus and circuitry for changing the power delivered from an electrosurgical generator.

Prior to the invention of the subject application, the capability of changing output power delivered from an electrosurgical generator has been provided by controls located at the keyboard or control panel of the generator. At the handpiece held by the surgeon, a capability has been provided of changing the mode of operation of the generator—that is, two switches have been employed at the handpiece where either the cut or coagulation mode of operation could be selected. This is a very convenient feature in that the surgeon can change the mode of operation while in the sterile field of the surgical procedure without having to return to the control panel of the generator, which is outside the sterile field. However, in order to effect a change in the level of the power delivered by the generator, it has been necessary to return to the generator to effect such a change. Since it would be very desirable to be able to also effect this type change in the sterile field, the apparatus of the prior art has had a shortcoming in this respect.

SUMMARY OF THE INVENTION

It is thus a primary object of this invention to provide, in electrosurgery, the capability of changing the power delivered by the generator, the change being effected in the sterile field, in addition to, at the control panel of the generator.

It is a further object of this invention to provide, at an electrosurgical handpiece, the capability of effecting changes in the generator output power.

It is a further object of this invention to provide an improved handpiece where functions such as coagulation, cutting, power increase and power decrease can be selected thereat while at the same time employing a minimal number of wires between the handpiece and the generator.

It is a further object of this invention to provide improved circuitry for decoding the signals transmitted from the handpiece in such a manner as to minimize the number of wires employed between the handpiece and the generator.

It is a further object of this invention to provide means for enabling the generator to determine whether the handpiece has the capability of changing the power level thereat.

It is a further object of this invention to provide the capability of changing the generator power output level in response to a request to do so from the handpiece.

It is a further object of this invention to provide the capability of determining whether the requested power increase or decrease exceeds a predetermined maximum or minimum.

Other objects and advantages of this invention will be apparent from a reading of the following specification and claims taken with the drawing.

BRIEF DESCRIPTION OF THE DRAWING

FIG. 1 is a block diagram illustrating in general an electrosurgical system.

FIG. 2 is a schematic diagram of an illustrative handpiece and the wires connected thereto in accordance with the present invention.

FIG. 4 is a truth table which illustrates the operation of the decoding circuitry of FIG. 3.

DETAILED DESCRIPTION OF A PREFERRED EMBODIMENT OF THE INVENTION

Figure 3:
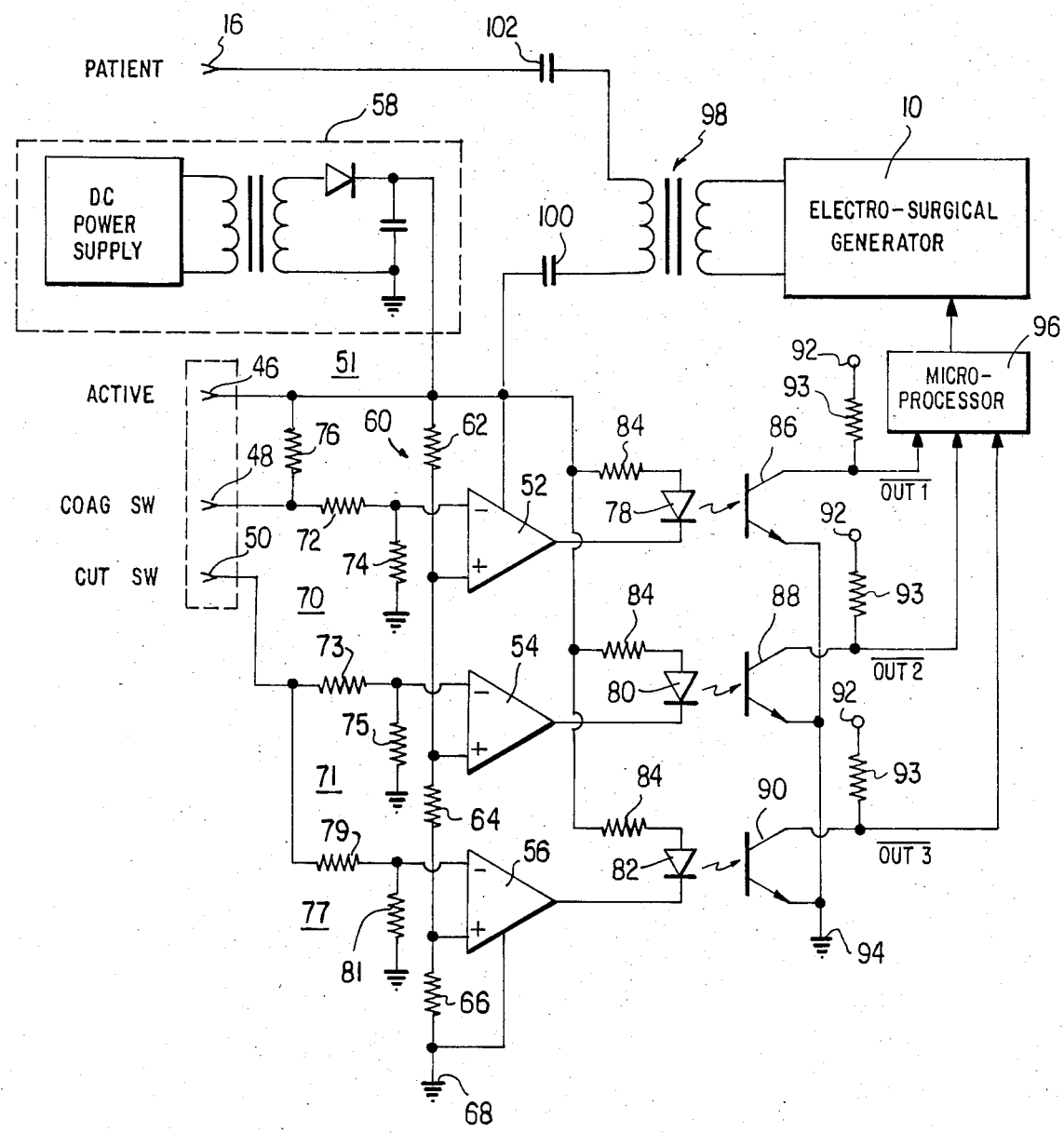
FIG. 3 is a schematic diagram of illustrative decoding circuitry in accordance with the present invention.

Reference should be made to the drawing where like reference numerals refer to like parts.

Referring to FIG. 1, there is illustrated a generalized electrosurgical system comprising a generator 10, a handpiece 12 having an active electrode 14, this electrode contacting the patient to effect either a cut or coagulation procedure depending upon the mode selected. Attached to the patient is a return electrode 16 which returns the electrosurgical current from the patient to generator 10.

Referring to FIG. 2, there is shown in more detail handpiece 12 with active electrode 14 connected thereto. The handpiece is connected by a cable 18 to generator 10 via a connector 20. Three wires or lines, 22, 24 and 26 pass through the cable where wire 22 conducts the electrosurgical current from the generator to the active electrode, this wire sometimes hereafter being referred to as the active line. This wire also conducts a DC voltage from the generator which is employed for mode selecting at handpiece 12, as is well known and is described in U.S. Pat. Nos. 3,699,967 and 3,801,800, both of which are incorporated herein by reference. A single pole, coagulation mode switch 28 and a single pole, cut mode switch 30 are provided at the handpiece the provision of such switches again being conventional as described in the above patents. Closure of coagulation mode switch 28 will return the above-mentioned DC signal applied to line 22 to the generator via line 24 to thereby signal to the generator a request to effect a coagulation mode of operation where line 24 is sometimes hereafter referred to as the coagulation line. In a similar manner, closure of cut mode switch 30 will effect the cut mode of operation where line 26 is sometimes hereafter referred to as the cut line.

In accordance with the present invention, two more switches are added to handpiece 12 to thereby provide the capability of incrementing or decrementing the output power level, this capability being present at the handpiece and thus in the sterile field. In particular, switch 32 connected between the coagulation and cut lines is employed to increment the power level, the increments typically being ten percent the power level last set at the control panel of generator 10 or one watt, whichever is greater, in a manner which will be described in more detail hereinafter. A double pole switch or functional equivalent, generally indicated at 34 having a first switching element 36 connected between the active and coagulation lines and a second switching element 38 connected between the coagulation and cut lines where the switching elements are ganged as indicated, provides decrementing of the output power level, the decrements typically being ten percent of the power level last set as the control panel or one watt, whichever is greater. Connector 20 includes connectors 40, 42 and 44 which are respectively connected to terminals 46, 48 and 50 of the decoding circuitry 51 of FIG. 3.

One functional equivalent (not shown) which may be employed in place of double pole switch 34 comprises a single pole switch having one terminal thereof connected to active line 22 and the other terminal thereof connected to the anodes of two diodes where the cathodes of the diodes are respectively connected to coagulation line 24 and cut line 26.

In the circuitry of FIG. 3 are provided three window comparators 52 through 56. Reference voltages for these comparators are applied to the positive terminals thereof, these reference voltages being derived from an isolated power supply 58 and a voltage dividing network 60 comprising resistors 62 through 66 connected between supply 58 and ground 68. The isolated power supply 58 is known and an example thereof is provided in U.S. Pat. No. 3,801,800. The voltage at terminal 48 is applied to the minus terminal of window comparator 52 via a voltage divider 70, which comprises resistors 70 and 72. The voltage at terminal 50 is applied to (a) the minus terminal of window comparator 54 via a voltage divider 71 comprising resistors 73 and 75 and (b) the minus terminal of window comparator 56 via a voltage divider 77 comprising resistors 79 and 81. The specific values of the resistors of voltage dividers 70, 71, and 77 may vary and thus the values of the D.C. signals applied to the comparators 52 through 56 may be different. A resistor 76 is provided from the active line to the coagulation line. The outputs of the comparators 52 through 56 are respectively applied to photodiodes 78 through 82 or like electrically responsive, light emitting elements, the photodiodes each being connected in series with a resistor 84 to the isolated power supply 58.

Photodiodes 78 through 82 are respectively optically coupled to phototransistors 86 through 90 or other like light responsive, switching elements where each of the transistors is connected to a voltage source 92 through a load resistor 93 and grounded at 94. The outputs of the phototransistors 86 through 90 are applied to a microprocessor 96, the processor having an output which is applied to electrosurgical generator 10 to control the power level thereof. In particular, the microprocessor, which may be an INTEL 8039, is programmed to be responsive to different combinations of outputs occurring at phototransistors 86 through 90 as will be described below with respect to FIGS. 5 through 9.

The output of generator 10 is applied to a transformer indicated at 98, the high side of the transformer secondary winding being applied through a capacitor 100 to active electrode 14 via terminal 46 while the low side thereof is connected to return electrode 16 via capacitor 102, the purpose of the capacitors being to remove the DC current and other low frequency currents from the circuit connected to the patient. Although electrosurgical generator 10 has been shown as a separate element in FIG. 3, in practice, transformer 98, decoding circuitry 51, and microprocessor 96 may be included in the generator.

Reference should now be made to the truth table of FIG. 4 which illustrates how decoding circuitry 51 of FIG. 3 decodes the various combinations of signals provided by switches 28 through 34 into other combinations of signals at the outputs of phototransistors 86 through 90 for processing by microprocessor 96. If none of the switches 28 through 34 is activated (that is closed), none of the reference voltages at comparators 52 through 56 will be exceeded and therefore none of the photodiodes 78 through 82 will be activated. Accordingly, none of the phototransistors 86 through 90 will be conducting and thus the voltages at the collectors of each of the phototransistors will be +V. Due to the type of logic employed, the output $\overline{OUT}$ 1 occurring at the collector of phototransistor 86, is considered to be logic one or off when its collector voltage is +V, this being shown in the table of FIG. 4. Since none of the phototransistors 86 through 90 are conducting, the outputs thereof are all off or logical ones.

Referring to the third entry in the table of FIG. 4, it is assumed coagulation mode switch 28 is closed, it being understood that only one of the switches 28 through 34 is closed at any particular moment of time—that is, these switches are each typically of the type which close when pressed and open upon release, such switches being well known in this art. When switch 28 is closed, terminal 48 of FIG. 3 is connected to the full output of isolated power supply 58 so that the voltage at the minus terminal of comparator 52 exceeds the reference potential established at the positive terminal of the comparator by the potential dividing network 60. Accordingly, a path is closed from power supply 58 through photodiode 78, and comparator 52 to ground to thus activate the photodiode. This in turn causes phototransistor 86 to conduct whereby a current path is established between the voltage source 92 for phototransistor 86 through the phototransistor to ground 94 whereby the output voltage of the phototransistor drops to a level near that of ground. Accordingly, in accordance with the foregoing logic, $\overline{OUT}$ 1 becomes zero which indicates this output is on. Thus, as can be seen in the table of FIG. 4 the combination of outputs occurring at phototransistors 86 through 90 is as shown. The outputs of phototransistors 88 and 90 are not switched since no voltage is applied to terminal 50 when coagulation mode switch 28 is closed.

It is next assumed cut mode switch 30 is closed, this being illustrated in the second entry of the FIG. 4 table. At this time the full voltage of isolated power supply 58 is applied to terminal 50. The voltage applied to the minus terminals of comparators 54 and 56 will be determined by the voltage at terminal 50 and the values of the resistors comprising voltage dividers 71 and 77. The voltages applied to these minus terminals will exceed the reference potential established at the positive terminal of comparator 54 by potential dividing network 60 and the reference potential established at the positive terminal of comparator 56 also by potential dividing network 60. Hence, both of these comparators are turned on to effect the energization of photodiodes 80 and 82. Moreover, the outputs of their associated phototransistors 88 and 90 are switched to thereby provide the combination of outputs indicated in the truth table.

Reference should now be made to the fourth entry in the table of FIG. 4 which indicates the combination of output signals which occurs when power increment switch 32 is closed. When this switch is closed, a path is established from isolated power supply 58 through resistor 76 (FIG. 3) and switch 32 (FIG. 2) to terminal 50 of FIG. 3. However, in this instance, the full voltage of the isolated power supply 58 is not applied to terminal 50; rather, the power supply voltage is dropped by an amount depending upon the size of resistor 76. The size of resistor 76 is so selected that the voltage occurring at the minus terminal of comparator 56 will exceed the reference potential at this comparator. However, the voltage occurring at the minus terminal of comparator 54 will not exceed the reference potential at this comparator. Thus, when switch 32 is closed, only photodiode 82 is activated to switch the output of phototransistor 90. Accordingly, as can be seen in FIG. 4, the combination of outputs occurring at phototransistors 86 through 90 is as indicated.

Referring now to the last entry in the table of FIG. 4, and in particular to the closure of power decrement switch 34, it can be seen that when this switch is closed, the full voltage of the isolated power supply is applied through switching elements 36 and 38 to both terminals 48 and 50 of FIG. 3. Accordingly, the reference voltages of all the comparators 52 through 56 are exceeded to thus energize all of the photodiodes 78 through 82. Hence, all of the outputs of phototransistors 86 through 90 are switched as indicated in the table of FIG. 4. It can thus be seen that the decoding circuitry 51 of FIG. 3 provides various combinations of outputs at the collectors of phototransistors 86 through 90 depending on which of the switches 28 through 34 is actuated at handpiece 12.

Figure 5:
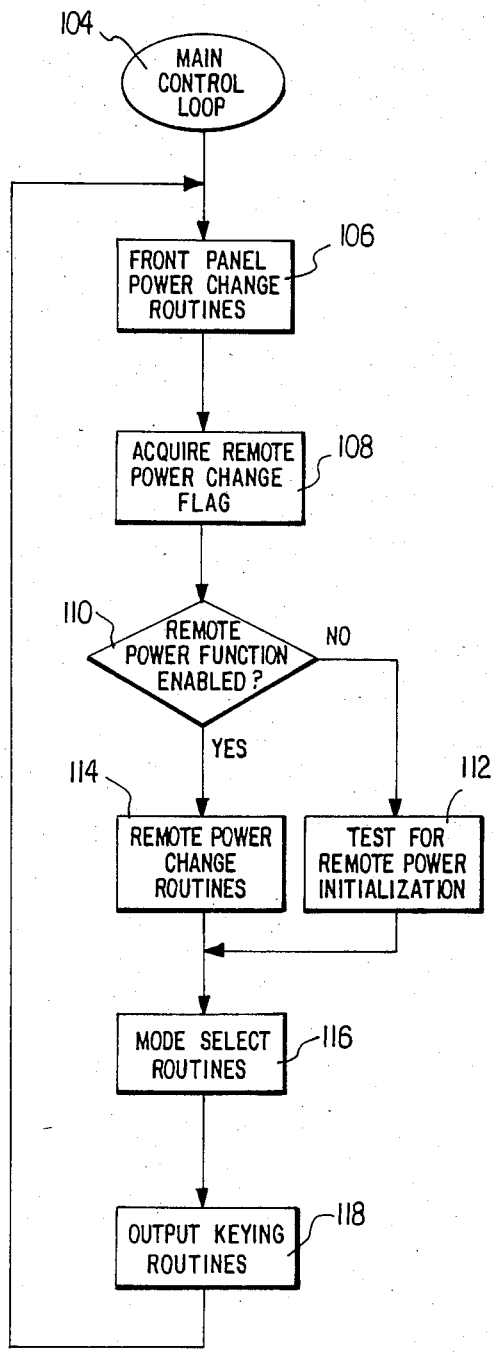
FIG. 5 is a flow chart of an illustrative main control loop of a computer program for use in the subject invention.
Figure 6:
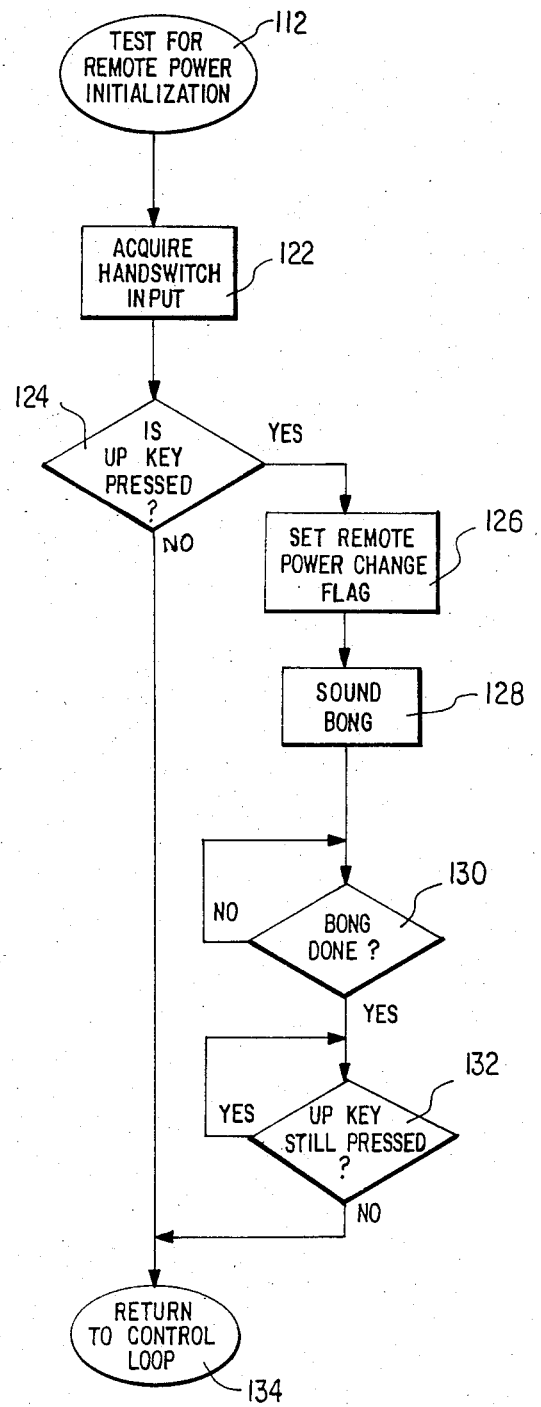
FIG. 6 is a flow chart of a subroutine of the main control loop of FIG. 5, this subroutine determining whether the remote power change capability of the present invention has been requested.
Figure 7:
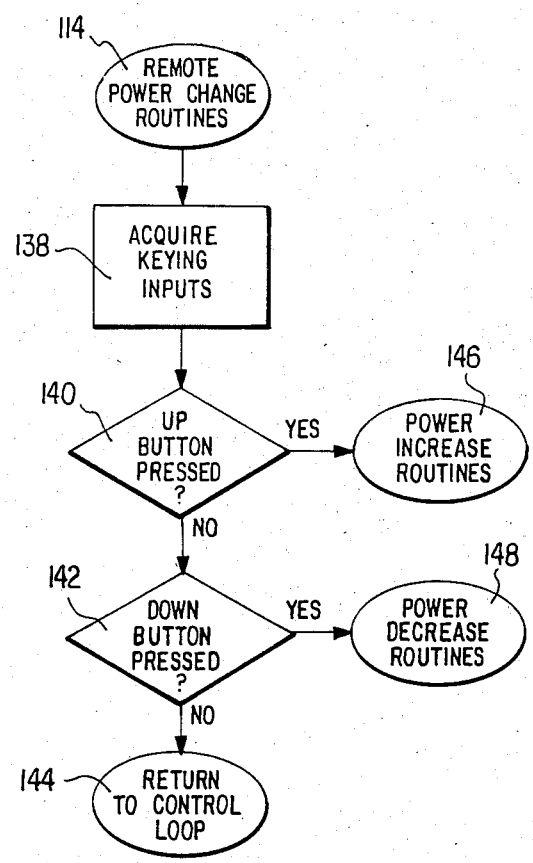
FIG. 7 is a flow chart of a subroutine which determines whether the power is to be increased or decreased.
Figure 9:
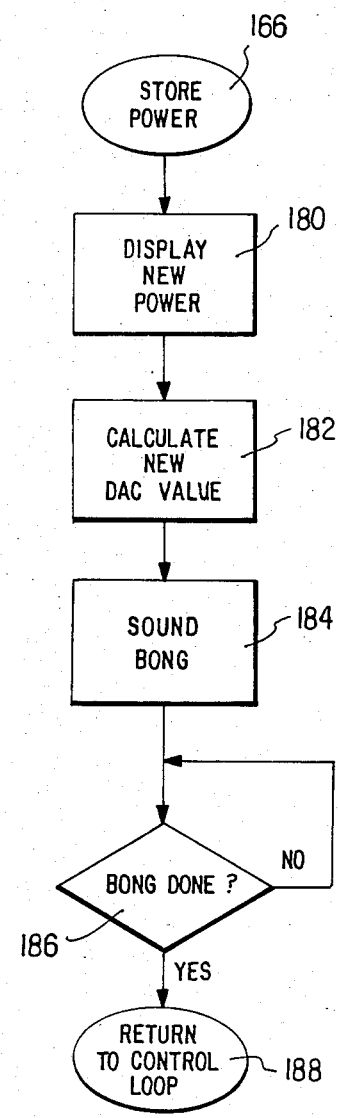
FIG. 9 is a flow chart of a subroutine which effects the requested power increase or decrease.

Reference should now be made to FIGS. 5 through 9 which illustrate various flow charts of an illustrative program and subroutines thereof which may be employed in microprocessor 96 to process the outputs of decoding circuit 51 and thus vary the control exercised by the surgeon in the sterile field. FIG. 5 is a flow chart of the main control loop of the program and FIGS. 6 through 9 are various subroutines which are entered either directly or indirectly from the main control loop of FIG. 5. In FIG. 5, the program first processes at block 106 any changes in the power level requested from the control panel. Changes requested from this source are as such not part of the present invention and thus are not further discussed. The program next acquires at block 108 the state of a flag which when set indicates a remote power change feature has been enabled—that is, that the accessory has been actuated in a way to indicate that it has the capability of signalling a request for an increase or decrease in power in accordance with the present invention. The manner of setting this flag will be described below with respect to FIG. 6. Once the contents of the flag have been acquired, the contents thereof are checked at 110 to determine whether the remote power function has been enabled. Assuming it has not been enabled, the program passes control to block 112 to test whether the remote power function is now being requested even though it was not initialized at the time the check at 110 was made. The flow chart for the test effected at block 112 is illustrated in FIG. 6. However, before proceeding to FIG. 6, the remainder of the functions executed by the main control loop of FIG. 5 will be briefly described. Thus, assuming the remote power function has been enabled as determined at 110, the program passes control to block 114 to test for and implement any requested remoted power change routines, these being described in further detail with respect to FIGS. 7 through 9. Once the power change has been effected, the main control loop moves to block 116 where it senses for and implements any change of the chosen mode of operation—that is, the specific type of coagulation or cutting desired. Finally, at block 118, the output is keyed and the power delivered to the patient, the parameters of the delivered power corresponding to those described above.

Reference should now be made to FIG. 6 which is the flow chart for testing whether the remote power change feature is to be enabled as indicated from the handpiece, this test occurring at 112 in the main control loop of FIG. 5. In FIG. 6, the hand switch input is acquired at 122—that is, the outputs of phototransistors 86 through 90 of FIG. 3 are sampled. At 124 a check is made to see whether switch 32 is being actuated. The test that is particularly made is whether the outputs of phototransistors 86 through 90 correspond to the settings shown in the fourth entry of the table of FIG. 4. If they do not, return to the main control loop occurs from 134 of FIG. 6 to 104 of FIG. 5. Assuming the up button 32 is being actuated, the remote power change flag is set to thereby indicate this fact. Thus, in accordance with an important aspect of the invention, up switch 32 must be actuated at the handpiece before the remote power change feature can be implemented. Of course, another switch provided on the handpiece could also permit initialization of this feature. Only after this initialization of the remote power changing feature has occurred will the system of the present invention operate in this mode. By providing this initialization feature, it is possible to use other handpieces which do not have a remote power changing capability and yet the remote power change of the present invention will not be inadvertently implemented since the above initialization procedure must be followed before it can be effected. Hence, compatability with other handpieces is provided. It should also be noted other means can be employed to implement the initialization of the remote power changing. For example, an additional pin or connector (not shown) may be provided on connector 20 and an additional terminal may be provided at interface circuit 51 whereby whenever this prong is present, it indicates the handpiece has the remote power changing capability. See U.S. Pat. No. 4,416,276, which is incorporated herein by reference, where pin actuated switch 51 serves a similar function for a different feature.

Once the remote power change flag has been set at block 126, a bong is sounded to alert the surgeon the remote power change feature has now been initialized and is ready to use. In this connection, it should be noted that the first actuation of the up switch 32 does not effect an incrementation of the output power but rather simply initializes this feature as discussed above. The program next moves to 130 where it loops until the bong is completed. It then moves to 132 where it again loops until the up switch 32 is released. At that time, it returns to main control loop 104 of FIG. 5 via 134.

At the main control loop, it again acquires the remote power change flag at 108. Now that this flag has been set at block 126 of FIG. 6, the test at 110 will be passed and the program will pass to the remote power change routines 114. In particular, referring to FIG. 7 the outputs of phototransistors 86 through 90 are once again acquired. A determination is then made at 140 to see if the up button 32 is being pressed. If not, a determination is then made to see if down button 34 is being pressed. If not, the program returns to the main control loop of FIG. 5 via 144 of FIG. 7. The main control loop of FIG. 5 is cycled through approximately 20 times per second until an input is sensed. Thus, when the program returns to 140 a fraction of a second later to determine if up button 32 has been pressed, it will be assumed that it is being pressed at this time.

Figure 8:
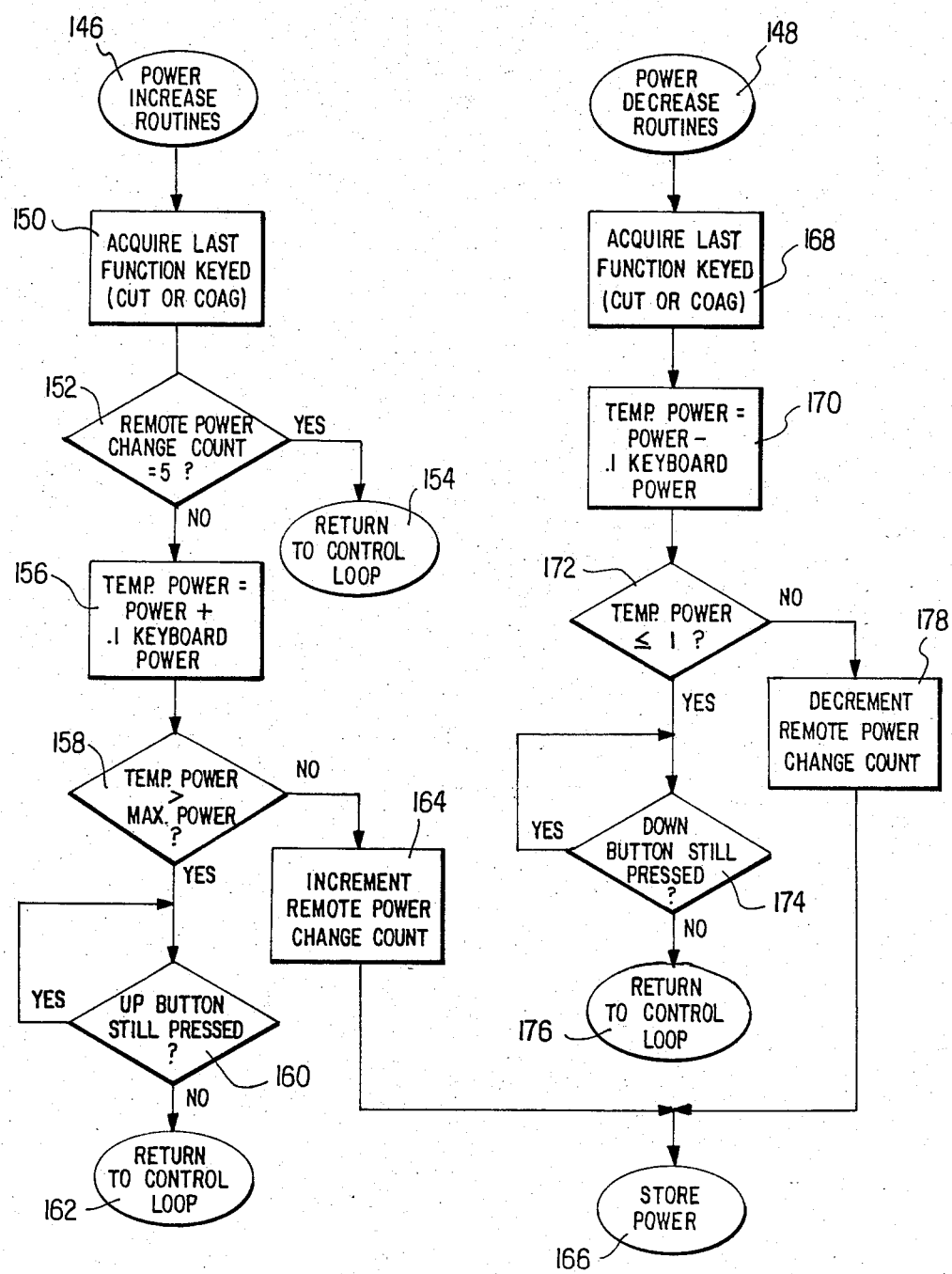
FIG. 8 is a flow chart of subroutines which preliminarily process requests for either a power increase or decrease.

Thus, program control is transferred via 146 to the power increase routine of FIG. 8. Next, at block 150 the last function keyed at the control panel of generator 10 is acquired—that is, a determination is made as to whether the coagulation or cut function was last activated. Next, at 152 a check is made to see whether or not more than five increments in power have been requested. In accordance with the present invention, no more than a predetermined number of increments in the output power is permitted when the increments are initiated from the sterile field. This number is chosen to be five in the present invention. Of course, other numbers may be employed depending upon the particular system. Once this number of power increments have been requested from the sterile field, the surgeon is required to return to the control panel to effect any further increase in the power setting if so desired. In this manner, the surgeon is given an additional amount of time to be certain the increased power requirement is needed. If the number of requested power increments is five, program control returns to the main control loop of FIG. 5 via 154. If the number of power increments is less than five, the power is increased at block 156 in the following manner. First, the current output power is obtained and then added to it is one-tenth of the keyboard power. By keyboard power it is meant the power setting last set at the control panel of the generator. For example, if the last output power level set at the control panel was 100 watts, and assuming the current output power of the generator is 130 watts (the power already having been incremented three times), one-tenth of the 100 watt setting (or 10 watts) would be added to the current output power to arrive at a temporary power of 140 watts.

Before this temporary power is accepted a test is made at 158 to determine whether this temporary power exceeds the maximum power permissible for the particular mode of operation the generator is presently in. Thus, for example in the cut mode the maximum permissible power might be 300 watts while for the coagulation mode it might be 120 watts. As long as the newly calculated temporary power does not exceed this maximum power, normal operation will continue. However, if it does exceed the maximum power, program control passes to 160 where a determination is made as to whether the up button or switch 32 is still being pressed. If it is, the program loops until it is released, at which time it returns to the control loop without effecting any increase in the output power.

Assuming the temporary power does not exceed the maximum power, program control is transferred to block 164 where the remote power change count is incremented. It is this count which is checked at 152. Next at 166 control is transferred to the store power routine of FIG. 9. Thus, assuming the new power is 140 watts, the new power is displayed at the control panel at 180 and a digital to analog converter value is calculated at 182 for later utilization by the generator when keyed to effect the actual change in the output power of the generator. This method of changing the output power level is known and corresponds to a method which is already employed to change the power level from the control panel. This change in output power may also be effected in many ways known to those having ordinary skill in this art. At 184, a bong is sounded to alert the operator that the power has been increased by a ten percent factor. At 186 the program loops until the bong is completed and then it returns to the main control loop of FIG. 5 via 188.

It should be noted, in accordance with the present invention, the increase in power is not a ten percent increase in the current power but rather the increase is ten percent of the power last set at the keyboard or control panel of the generator. If the power were increased by ten percent of the current power, certain difficulties could arise. For example, suppose the initial power setting is 100 watts and the increments are ten percent of the current output power. Hence, the first increase would increment the output power to 110 watts. The next increment would increase it to 121 watts. If the power were now decremented by ten percent, it would be decreased to about 109 watts and a further decrement would decrease it to about 98 watts. Hence, it can be seen that, although the initial power was 100 watts, the power, after two increases of ten percent each and two decreases of ten percent, is 98 watts. The operator would expect that the power to return to the initial power after such a sequence. To avoid this difficulty, the procedure of the present invention is employed where the keyboard power (that is, the last output power set at the control panel of the generator) is employed as a reference point for subsequent changes in power. Although these changes have been described in terms of ten percent increments or decrements, the percentage change may be, of course, other than ten percent. Further, the percentage change may vary from step to step if so desired.

In summary, if the initial power setting from the keyboard or control panel of the generator is 100 watts and the surgeon increases that power from the hand switch to 150 watts by five ten percent increments, he can effect no further increases from the handpiece and must return to the keyboard to change the power setting thereat. Assume he changes the setting to 200 watts at the control panel. If he then subsequently increments the power by a ten percent factor, the power increase will be 20 watts since the last output power set at the control panel was 200 watts. It will not be 10 watts which is ten percent of the original output power setting at the control panel.

Returning to FIG. 7 and, in particular the remote power change routine 114, it was assumed the up button 32 had been pressed and thus the routine of FIG. 8 was entered at 146. However, if the down button is pressed thereby indicating a desire on the part of the surgeon to decrease the power by ten percent, this will be determined at 142 whereby the routine of FIG. 8 is entered at 148 to effect the power decrease. At block 168, the last function keyed (cut or coagulation) is acquired. Next, the temporary power is calculated by subtracting from the current power one-tenth of the keyboard power (again, the output power level last set at the keyboard or control panel of the generator). A test is then made at 172 to determine if the temporary power is less than or equal to one watt. If it is, the routine aborts and returns to the main control loop of FIG. 5. This is done after the test at 174 is passed to determine if the down button is still pressed. There the program loops until this button is released whereafter it does return to the main control loop.

If the temporary power is not less than or equal to one watt, program control transfers to block 178 where the remote power change count is decremented by one. Thus, assuming that the initial output power level was set at the control panel to 100 watts, it is possible to increment the power level four times to 140 watts and then decrement it three times to 110 watts followed by three more increments back to 140 watts. As can be seen, the increment function has been executed seven times in this sequence and yet the remote power change count, as tested at 152, will not have exceeded five because this count was decremented three times in the foregoing illustrative sequence. Only when the surgeon attempts to change the output level to 150 watts will the test at 152 not be passed. Thus, as stated above, this test ensures that the surgeon can effect only so much increase in the output power from the sterile field before he must return to the control panel to effect a further increase. The number of power decreases is limited only by the minimum power level of one watt—any request for power decrease which would result in less than one watt of power would not be processed. Once the power has been decremented at 178, control is transferred to the store power routine of FIG. 9 where the actual power delivered to the patient is decremented at that time as described above.

Although the present invention has been described in terms of the direct transmission of an electrical signal from the sterile field to the generator, it is to be understood other signals such as optical, ultrasound, etc. may also be transmitted in the foregoing manner. Moreover, other signal transmission arrangements may also be employed such as a wire(s) connected at one end to the generator and dedicated to power output changes where, in the sterile field, a power changing switching device would be connected to the other end of the wire and where the switching device may or may not be located at handpiece 12. Another signal transmission arrangement which might be employed comprises a switch operated transmitter which may or may not be located at the handpiece to thus transmit the signals(s) by wireless transmission. Furthermore, although three lines are employed in the above described embodiment for transmitting the mode and power change information from the handpiece, a two wire arrangement may also be employed where different resistors or resistor combinations corresponding to the different items of information to be transmitted may be placed across the two lines and switched in depending on the item of information to be transmitted. Thus, associated with each item would be a different voltage level which could be detected at the generator.

It is to be understood that the above detailed description of the various embodiments of the invention is provided by way of example only. Various details of design and construction may be modified without departing from the true spirit and scope of the invention as set forth in the appended claims.

What is claimed is:

1. An electrosurgical generating system comprising:
an electrosurgical generator;
a handpiece including (a) an active electrode connected to said generator for applying electrosurgical current from the generator to a patient and (b) power changing means for changing the level of output power delivered from the generator to the patient; and
initializing means responsive to said power changing means for making an initial determination that said handpiece includes said power changing means and thus permit said power changing means to change said output power level only if said handpiece includes said power changing means.

2. A system as in claim 1 where said means for changing the output power level of the generator includes a pair of switches, one power increment switch for effecting an increase in the output power level of the generator and the other a power decrement switch for effecting a decrease thereof.

3. A system as in claim 2 where said initializing means includes one of said switches.

4. A system as in claim 3 where said initializing means includes said power increment switch.

5. A system as in claim 1 including means for preventing changes in the output power once the power has been changed a predetermined amount.

6. A system as in claim 1 including means for changing the output power level of the generator by a plurality of successive, incremental amounts.

7. A system as in claim 6 including further power changing means for changing the output power level of the generator, said further means being disposed at the generator and where said means for changing said output level by a plurality of incremental amounts includes means for incrementing the current output power level by a predetermined percentage of the power level last set by the further power changing means at the electrosurgical generator.

8. A system as in claim 7 where said means for incrementing the current output power level by a predetermined percentage includes means for establishing said predetermined percentage as ten percent.

9. An electrosurgical generating system comprising:
an electrosurgical generator;
a handpiece including an active electrode connected to said electrosurgical generator for applying electrosurgical current from the generator to a patient, said handpiece having means disposed thereat for changing the level of the output power delivered from said generator to said patient;
initializing means responsive to said power changing means for making an initial determination that said handpiece includes said power changing means and thus permit said power changing means to change said output power level only if said handpiece includes said power changing means;
means for changing the output power level of the generator by a plurality of successive, incremental amounts;

means for preventing changes in the output power level once the power has been changed a predetermined amount by said power changing means; and further power changing means for changing the output power level of the generator, said further means being disposed at the generator and where said means for changing said output power level by a plurality of incremental amounts includes means for incrementing the current output power level by a predetermined percentage of the power level last set by the further power changing means at the electrosurgical generator.

* * * * *